United States Patent [19]
Kazami et al.

[11] Patent Number: 5,604,123
[45] Date of Patent: Feb. 18, 1997

[54] LUCIFERASE, GENE ENCODING THE SAME AND PRODUCTION PROCESS OF THE SAME

[75] Inventors: Jun Kazami; Haruji Nakamura, both of Shiga; Toshio Goto, deceased, late of Nagoya, all of Japan, by Izumi Goto, Kaoru Goto, legal representatives

[73] Assignee: Toray Industries, Inc., Tokyo, Japan

[21] Appl. No.: 260,042

[22] Filed: Jun. 15, 1994

Related U.S. Application Data

[63] Continuation-in-part of Ser. No. 930,486, Aug. 14, 1992, abandoned, which is a continuation of Ser. No. 469,479, filed as PCT/JP89/00811, Aug. 9, 1989 published as WO90/01542, Feb. 22, 1990, abandoned.

[30] Foreign Application Priority Data

Aug. 9, 1988 [JP] Japan .................... 63-199295
Aug. 17, 1988 [JP] Japan .................... 63-204173

[51] Int. Cl.$^6$ ............... C12N 15/35; C12N 15/63; C12N 15/70; C12N 15/79
[52] U.S. Cl. ............ 435/189; 435/69.1; 435/252.3; 435/252.33; 435/320.1; 536/23.2; 935/14; 935/29; 935/69; 935/73
[58] Field of Search ................. 435/189, 69.1, 435/252.3, 252.33, 320.1; 536/23.2

[56] References Cited

U.S. PATENT DOCUMENTS

4,546,082  10/1985  Kurjan et al. .................... 435/172.3
4,968,613  11/1990  Masuda et al. .................... 435/172.3

FOREIGN PATENT DOCUMENTS

0318915  6/1988  European Pat. Off. .
4-258288  9/1992  Japan .................... 435/193

OTHER PUBLICATIONS

Biochemistry, vol. 13, No. 25, 1974, pp. 5204–5209; F. I. Tsuji et al.: "Some properties of luciferase from the bioluminescent crustacean, Cypridina hilgendorfili".
de Wet, J. R., et al., 1987, Molecular and Cellular Biology, 7(2):725–737.
Tsaji, F. I., 1978, Methods in Enzymology, 57: 364–372.
Johnston, M., et al., 1984, Molecular and Cellular Biology, 4:1440–1448.
Johnson, F. H., et al., 1978, Methods in Enzymology 57: 331–363.
de Wet, J. R., et al., 1985, Proc. Natl'l. Acad. Sci., USA, 82:7870–7873.
Eantage, J. S., et al., 1983, Proc. Nat'l. Acad. Sci. USA 80: 3671–3675.
Briggs, M. S., et al., 1986, in Advances in Protein Chemistry, 38: 109–135, Academic Press, Inc.
Suggs, S. V., et al., 1981, Proceedings, National Academy of Sciences, USA, 78(11):6613–6617.
Jaye, M., et al., 1983, Nucleic Acids Research 11(8): 2325–2335.
Thompson, E. M., et al., 1989, Proceedings, National Academy of Sciences, USA 86: 6567–6571.
Inouye, S., et al., 1985, Proceedings of the National Academy of Sciences, U.S.A., 82(10):3154–3158.
Prasher, D. L., et al., 1986, Methods in Enzymology, 133:288–298.
Noguchi, M., et al., 1986, Methods in Enzymology, 133: 298–306.

*Primary Examiner*—Robert A. Wax
*Assistant Examiner*—William W. Moore
*Attorney, Agent, or Firm*—White & Case

[57] ABSTRACT

The present invention provides luciferase with an amino acid sequence shown in FIG. 1, a gene encoding the the same, a recombinant vector DNA comprising the gene ligated at a site downstream of a promoter which can be expressed in a host cell, a transformant prepared by transforming the host cell with the recombinant vector DNA and a process of producing luciferase using the transformant.

6 Claims, 9 Drawing Sheets

```
                                    10                                                    20
Met Lys Leu Ile Ile Leu Ser Ile Ile Leu Ala Tyr Cys Val Thr Val Asn Cys Gln Asp
ATG AAG CTA ATA ATT CTG TCT ATT ATA TTG GCC TAC TGT GTC ACA GTC AAC TGC CAG GAT
         10          20          30          40          50          60

30                                                    40
Ala Cys Pro Val Glu Ala Glu Ala Pro Ser Ser Thr Pro Thr Val Pro Thr Ser Cys Glu
GCA TGT CCT GTA GAA GCT GAA GCA CCG TCA AGT ACA CCA ACA GTC CCA ACA TCT TGT GAA
         70          80          90         100         110         120

50                                                    60
Ala Lys Glu Gly Glu Cys Ile Asp Thr Arg Cys Ala Thr Cys Lys Arg Asp Ile Leu Ser
GCT AAA GAA GGA GAA TGT ATC GAT ACC AGA TGC GCA ACA TGT AAA CGA GAC ATA CTA TCA
        130         140         150         160         170         180

70                                                    80
Asp Gly Leu Cys Glu Asn Lys Pro Gly Lys Thr Cys Cys Arg Met Cys Gln Tyr Val Ile
GAC GGA CTG TGT GAA AAT AAA CCA GGG AAG ACA TGC TGT AGA ATG TGC CAG TAT GTA ATT
        190         200         210         220         230         240

90                                                   100
Glu Cys Arg Val Glu Ala Ala Gly Tyr Phe Arg Thr Phe Tyr Gly Lys Arg Phe Asn Phe
GAA TGC AGA GTA GAA GCT GCT GGA TAT TTT AGA ACG TTT TAC GGC AAA AGA TTT AAT TTT
        250         260         270         280         290         300

110                                                   120
Gln Glu Pro Gly Lys Tyr Val Leu Ala Arg Gly Thr Lys Gly Gly Asp Trp Ser Val Thr
CAG GAA CCT GGT AAA TAT GTG CTG GCT CGA GGA ACC AAG GGT GGC GAC TGG TCT GTA ACC
        310         320         330         340         350         360

130                                                   140
Leu Thr Met Glu Asn Leu Asp Gly Gln Lys Gly Ala Val Leu Thr Lys Thr Thr Leu Glu
CTC ACC ATG GAG AAT CTA GAT GGA CAG AAG GGA GCT GTA CTG ACT AAG ACA ACA CTG GAG
        370         380         390         400         410         420

150                                                   160
Val Val Gly Asp Val Ile Asp Ile Thr Gln Ala Thr Ala Asp Pro Ile Thr Val Asn Gly
GTA GTA GGA GAC GTA ATA GAC ATT ACT CAA GCT ACT GCA GAT CCT ATC ACA GTT AAC GGA
        430         440         450         460         470         480
```

FIG. 1a

```
                                       170                                        180
Gly Ala Asp Pro Val Ile Ala Asn Pro Phe Thr Ile Gly Glu Val Thr Ile Ala Val Val
GGA GCT GAC CCA GTT ATC GCT AAC CCG TTC ACA ATT GGT GAG GTG ACC ATT GCT GTT GTC
        490         500         510         520         530         540

190                                        200
Glu Ile Pro Gly Phe Asn Ile Thr Val Ile Glu Phe Phe Lys Leu Ile Val Ile Asp Ile
GAA ATA CCC GGC TTC AAT ATT ACA GTC ATC GAA TTC TTT AAA CTA ATC GTG ATT GAT ATT
        550         560         570         580         590         600

210                                        220
Leu Gly Gly Arg Ser Val Arg Ile Ala Pro Asp Thr Ala Asn Lys Gly Leu Ile Ser Gly
CTG GGA GGA AGA TCT GTG AGA ATT GCT CCA GAC ACA GCA AAC AAA GGA CTG ATA TCT GGT
        610         620         630         640         650         660

230                                        240
Ile Cys Gly Asn Leu Glu Met Asn Asp Ala Asp Asp Phe Thr Thr Asp Ala Asp Gln Leu
ATC TGT GGT AAT CTG GAG ATG AAT GAC GCT GAT GAC TTT ACT ACA GAC GCA GAT CAG CTG
        670         680         690         700         710         720

250                                        260
Ala Ile Gln Pro Asn Ile Asn Lys Glu Phe Asp Gly Cys Pro Phe Tyr Gly Asn Pro Ser
GCG ATC CAA CCC AAC ATA AAC AAA GAG TTC GAC GGC TGC CCA TTC TAC GGG AAT CCT TCT
        730         740         750         760         770         780

270                                        280
Asp Ile Glu Tyr Cys Lys Gly Leu Met Glu Pro Tyr Arg Ala Val Cys Arg Asn Asn Ile
GAT ATC GAA TAC TGC AAA GGT CTC ATG GAG CCA TAC AGA GCT GTA TGT CGT AAC AAT ATC
        790         800         810         820         830         840

290                                        300
Asn Phe Tyr Tyr Tyr Thr Leu Ser Cys Ala Phe Ala Tyr Cys Met Gly Gly Glu Glu Arg
AAC TTC TAC TAT TAC ACT CTG TCC TGC GCC TTC GCT TAC TGT ATG GGA GGA GAA GAA AGA
        850         860         870         880         890         900

310                                        320
Ala Lys His Val Leu Phe Asp Tyr Val Glu Thr Cys Ala Ala Pro Glu Thr Arg Gly Thr
GCT AAA CAC GTC CTT TTC GAC TAT GTT GAG ACA TGC GCT GCA CCG GAA ACG AGA GGA ACG
        910         920         930         940         950         960
```

FIG. 1b

```
                              330                                              340
Cys Val Leu Ser Gly His Thr Phe Tyr Asp Thr Phe Asp Lys Ala Arg Tyr Gln Phe Gln
TGT GTT TTA TCA GGA CAT ACT TTC TAT GAC ACA TTC GAC AAA GCC AGA TAT CAA TTC CAG
        970         980         990        1000        1010        1020

350                                              360
Gly Pro Cys Lys Glu Leu Leu Met Ala Ala Asp Cys Tyr Trp Asn Thr Trp Asp Val Lys
GGC CCA TGC AAA GAG CTT CTG ATG GCC GCA GAC TGT TAC TGG AAC ACA TGG GAT GTA AAG
       1030        1040        1050        1060        1070        1080

370                                              380
Val Ser His Arg Asp Val Glu Ser Tyr Thr Glu Val Glu Lys Val Thr Ile Arg Lys Gln
GTT TCA CAT AGA GAT GTT GAG TCA TAC ACT GAG GTA GAG AAA GTA ACA ATC AGG AAA CAG
       1090        1100        1110        1120        1130        1140

390                                              400
Ser Thr Val Val Asp Leu Ile Val Asp Gly Lys Gln Val Lys Val Gly Gly Val Asp Val
TCA ACT GTA GTA GAT TTG ATT GTG GAT GGC AAG CAG GTC AAG GTT GGA GGA GTG GAT GTA
       1150        1160        1170        1180        1190        1200

410                                              420
Ser Ile Pro Tyr Ser Ser Glu Asn Thr Ser Ile Tyr Trp Gln Asp Gly Asp Ile Leu Thr
TCT ATC CCG TAC AGT TCT GAG AAC ACA TCC ATA TAC TGG CAG GAT GGA GAC ATC CTG ACG
       1210        1220        1230        1240        1250        1260

430                                              440
Thr Ala Ile Leu Pro Glu Ala Leu Val Val Lys Phe Asn Phe Lys Gln Leu Leu Val Val
ACG GCC ATC CTA CCT GAA GCT CTT GTC GTT AAG TTC AAC TTT AAG CAG CTC CTT GTA GTT
       1270        1280        1290        1300        1310        1320

450                                              460
His Ile Arg Asp Pro Phe Asp Gly Lys Thr Cys Gly Ile Cys Gly Asn Tyr Asn Gln Asp
CAT ATC AGA GAT CCA TTC GAT GGA AAG ACA TGC GGC ATA TGT GGT AAC TAT AAT CAA GAT
       1330        1340        1350        1360        1370        1380

470                                              480
Ser Thr Asp Asp Phe Phe Asp Ala Glu Gly Ala Cys Ala Leu Thr Pro Asn Pro Pro Gly
TCA ACT GAT GAT TTC TTT GAC GCA GAA GGA GCA TGC GCT CTG ACC CCC AAT CCC CCA GGA
       1390        1400        1410        1420        1430        1440
```

FIG. 1c

```
                                        490                                               500
Cys Thr Glu Glu Gln Lys Pro Glu Ala Glu Arg Leu Cys Asn Ser Leu Phe Asp Ser Ser
TGT ACA GAG GAG CAG AAA CCA GAA GCT GAG CGA CTC TGC AAT AGT CTA TTT GAT AGT TCT
        1450        1460        1470        1480        1490        1500

510                                               520
Ile Asp Glu Lys Cys Asn Val Cys Tyr Lys Pro Asp Arg Ile Ala Arg Cys Met Tyr Glu
ATC GAC GAG AAA TGT AAT GTC TGC TAC AAG CCT GAC CGT ATT GCA CGA TGT ATG TAC GAG
        1510        1520        1530        1540        1550        1560

530                                               540
Tyr Cys Leu Arg Gly Gln Gln Gly Phe Cys Asp His Ala Trp Glu Phe Lys Lys Glu Cys
TAT TGC CTG AGG GGA CAG CAA GGA TTC TGT GAC CAT GCT TGG GAG TTC AAA AAA GAA TGC
        1570        1580        1590        1600        1610        1620

550                  555
Tyr Ile Lys His Gly Asp Thr Leu Glu Val Pro Pro Glu Cys Gln ***
TAC ATA AAG CAT GGA GAC ACT CTA GAA GTA CCA CCT GAA TGC CAA TAAATGAACAAAGATACAG
        1630        1640        1650        1660        1670        1680

AAGCTAAGACTACTACAGCAGAAGATAAAAGAGAAGCTGTAGTTCTTCAAAAACAGTATATTTTGATGTACTCATTGTT
    1690        1700        1710        1720        1730        1740        1750        1760

1770        1780        1790        1800        1810        1820
TACTTACATAAAAATAAATTGTTATTATCATAACGTAAAGAAAAAAAAAAAAAAAAAAA
```

FIG. Id

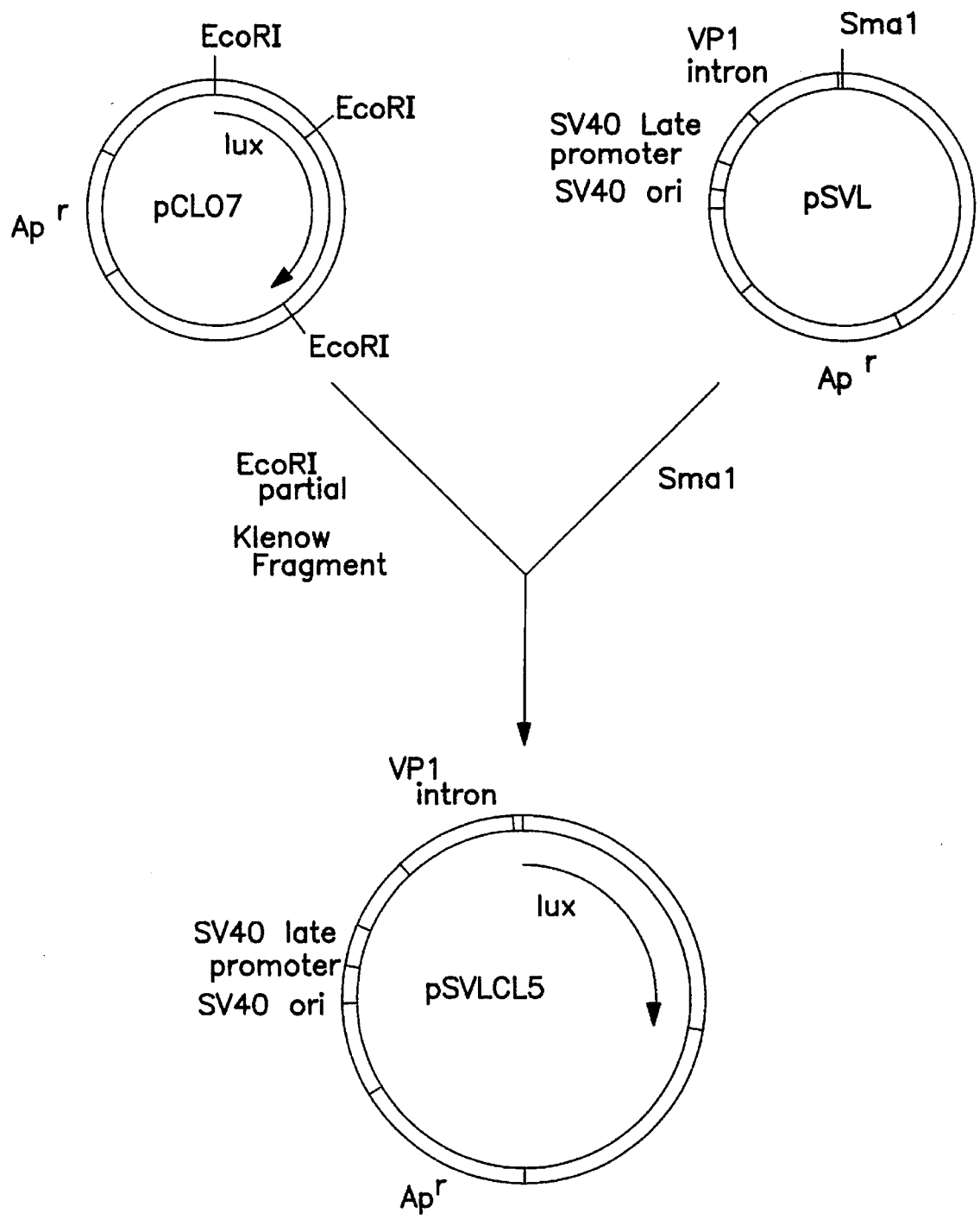

|     |         |             |       | 29  | 30  | 31  | 32  | 33  |     |
|-----|---------|-------------|-------|-----|-----|-----|-----|-----|-----|
| (a) | pMFE3A  | Met . . . . Lys | Arg | Pro | Ser | Ser | Thr | Pro | . . . |
| (b) | pMFE3B  | Met . . . . Lys | Arg | --- | --- | Ser | Thr | Pro | . . . |
| (c) | pMFE3C  | Met . . . . Lys | Arg | --- | --- | --- | Thr | Pro | . . . |
| (d) | 'pMFE3D | Met . . . . Lys | Arg | --- | Ser | Ser | Thr | Pro | . . . |

LUCIFERASE, GENE ENCODING THE SAME AND PRODUCTION PROCESS OF THE SAME

This application is a continuation-in-part of application Ser. No. 07/930,486, filed on Aug. 14, 1992, now abandoned, which is a continuation of application Ser. No. 07/469,479, filed as PCT/JP89/00811, Aug. 9, 1989, published as WO90/01542, Feb. 22, 1990, now abandoned.

TECHNICAL FIELD

This invention relates to a purified enzyme luciferase and a gene coding for the enzyme. This invention further provides a novel recombinant vector DNA in which the gene is inserted, a transformant containing the vector DNA, and a process of producing luciferase using the transformant.

BACKGROUND ART

*Cypridina hilgendorfii* is a marine ostracod crustacean living in the coast of the Sea of Japan, which releases a pale blue luminescent fluid when it is disturbed. The luminescence is produced by the oxidation of luciferin by an enzyme luciferase. The application of this luminescent system to the assay of a component contained in a sample in a trace amount is expected.

However, although luciferin can be chemically synthesized in a large amount, luciferase cannot be chemically synthesized because it is an enzyme, so that it is difficult to obtain luciferase in a large amount. This situation is also true in the case of luciferase of *Cypridina hilgendorfii* and highly purified luciferase of *Cypridina hilgendorfii* has not yet been obtained. Further, because of sea pollution, the catch of *Cypridina hilgendorfii* has drastically decreased. Thus, the constant supply of the luciferase of *Cypridina hilgendorfii* is not assured. Therefore, it is desired to establish a large scale production process of the enzyme, which employs the genetic recombination technique.

The object of the present invention is to attain the synthesis of highly purified luciferase by chemical synthesis process or by genetic recombination process, to provide a gene encoding the protein, to attain the expression of the cloned gene in an animal cell, yeast cell, in *E. coli* cell or the like, and to produce the highly purified enzyme in a large amount using the cell.

DISCLOSURE OF THE INVENTION

The present invention provides luciferase with an amino acid sequence shown in FIG. 1, a gene encoding the amino acid sequence, a novel recombinant vector containing the gene, a transformant prepared by transforming a host cell with the recombinant vector, and a process of producing luciferase using the transformant.

BRIEF DESCRIPTION OF THE DRAWINGS

FIGS. 1a, 1b, 1c and 1d show the nucleotide sequence of the luciferase from *Cypridina hilgendorfii* as well as the amino acid sequence thereof. The upper row in each line indicates the amino acid sequence and the lower row in each line indicates the nucleotide sequence of the cDNA.

FIG. 3 shows a construction of an expression vector pSVLCL5 of the luciferase from *Cypridina hilgendorfii* for animal cells.

BEST MODE FOR CARRYING OUT THE INVENTION

Figure 2:
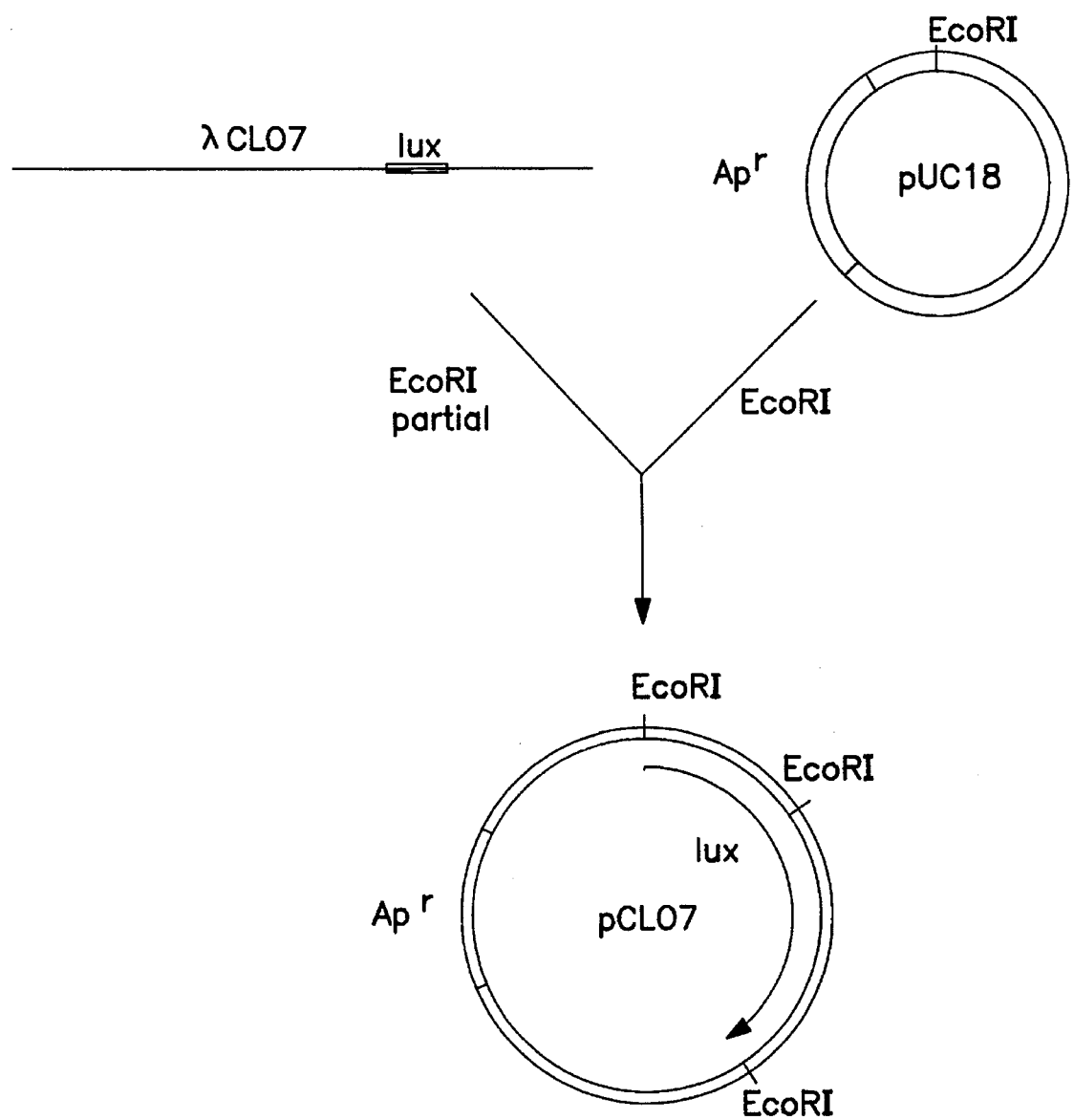
FIG. 2 shows a construction of a recombinant plasmid pCL07 containing the cDNA encoding the luciferase from *Cypridina hilgendorfii* as well as the restriction map thereof.

The luciferase of the present invention is a protein containing 555 amino acids having an amino acid sequence of 1st to 555th amino acid in the amino acid sequence shown in FIG. 1, a protein containing 527 amino acids having an amino acid sequence starting from the 29th amino acid proline in FIG. 1, a protein containing 526 amino acids having an amino acid sequence starting from the 30th amino acid serine in FIG. 1, a protein containing 525 amino acids having an amino acid sequence starting from the 31st amino acid serine, or a protein containing 524 amino acids having an amino acid sequence starting from the 32nd amino acid threonine. Further, proteins having the same amino acid sequence of the above-mentioned proteins except for some substitution, deletion and/or insertion are included in the scope of the present invention as long as they retain substantially the same luciferase activity. That is, luciferase equivalents are included in the scope of the present invention.

The gene of the present invention is a gene encoding the above-described luciferase and has a DNA sequence shown in the lower row in FIG. 1. The DNAs having some substitution, deletion and/or insertion of the DNA sequence shown in FIG. 1 are also included within the scope of the present invention as long as substantially the same luciferase activity is retained.

The procedure of obtaining the gene encoding the luciferase of the present invention will now be described. First, *Cypridina hilgendorfii* are disrupted in guanidine thiocyanate solution and total RNAs are extracted therefrom, followed by purification of poly(A)$^+$ RNAs by oligo(dT) cellulose column chromatography. After synthesizing cDNAs using the poly(A)$^+$ RNAs, the cDNAs are cloned into λ gt10 to obtain a cDNA library.

On the other hand, the amio acid sequence of the region in the vicinity of the N-terminal of the luciferase protein purified from *Cypridina hilgendorfii* and the amino acid sequences of the oligopeptides obtained by digestion with lysylendopeptidase are determined and several oligonucleotides having nucleotide sequences corresponding to the determined sequences are chemically synthesized. These oligonucleotides are used as probes for screening of the above-described cDNA library.

The nucleotide sequence of the inserted gene in the recombinants which form a hybrid with the probes in the plaque hybridization is determined. If it matches with the amino acid sequence of the luciferase protein, the inserted gene can be identified as a portion of the gene encoding the luciferase protein.

The present invention also provides recombinant vector DNAs containing the above-described DNA ligated at a site downstream of a promoter by which the gene can be expressed in a host cell such as animal cells, yeast cells and *E. coli* cells, the transformants transformed with the recombinant vector DNAs and processes of producing luciferase using the transformants.

More particularly, the recombinant vector DNAs of the present invention may be obtained by ligating the cDNA encoding the luciferase from *Cypridina hilgendorfii* with a vector DNA which is stably maintained in animal cells, yeast cells or *E. coli* cells, which vector DNA contains a promoter by which the inserted gene can be expressed in the host cells.

The promoter is a signal for initiating the RNA synthesis, which is recognized by RNA polymerase and bound thereby. The DNA sequence downstream from the promoter is transcribed to mRNA. Thus, in order that the gene encoding the luciferase from *Cypridina hilgendorfii* is transcribed to mRNA, it is necessary that the gene be located downstream of the promoter which functions in a host cell.

Thus, the recombinant vectors prepared by cleaving a vector DNA at an appropriate site downstream of the promoter contained in the vector and inserting therein the DNA containing the gene encoding the luciferase may be utilized.

The promoter which is used herein may be any promoter as long as it functions in a host cell. For example, promoters of animal genes and animal virus genes may be used for construction of the recombinant vector which functions in an animal cell. More particularly, examples of the promoters include SV40 late promoter, promoter of thymidine kinase gene, SV40 early promoter, promoter of Cytomegalovirus and the like. For yeast cells, promoters of yeast genes may be employed. For example, promoters of repressible acid phosphatase gene (PH05), galactokinase gene (GAL1), α pheromone gene (MFα1) gene of yeast and the like may be employed. For *E. coli*, promoters of *E. coli* genes and *E. coli* phages may be employed. For example, the promoter of lactose operon (lac), the try operon promoter, the $P_L$ promoter of λ phage and the like may be employed. Further, synthetic tac promoter and the like may also be employed.

Any vector DNA which is stably maintained in a host cell and which has a promoter which functions in the host cell may be employed. For example, for animal cells, plasmid vectors and virus vectors may be employed. More particularly, pSV2 (a vector containing SV40 early promoter, J. Mol. Appl. Genet. USA, 1, 327 (1982)), pSVL (a vector containing SV40 late promoter, commercially available from Pharmacia) and the like may be employed. For yeast cells, pMFα8 (a vector containing the promoter of the α pheromone gene (MFα1), Gene, 3, 155 (1985)), pAM85 (a vector containing the promoter of repressible acid phosphatase gene (PH05), Proc. Natl. Acad. Sci. USA, 80, 1 (1983)) and the like may be employed. For *E. coli*, pMT-1 (originated from an expression vector pKM6 containing the promoter of trp operon (Japanese Laid Open Patent Application (Kokai) No. 61-247387), pUC18/pUC19 (Gene, 33, 103 (1985)) and the like may be employed.

By inserting the cDNA encoding luciferase downstream of a nucleotide sequence encoding a signal peptide for protein secretion, which functions in the host cell, luciferase can be secreted to the outside of the cell. The signal sequence is not restricted to a specific one and the signal sequence of interleukin-2 (IL-2), for example, may be employed for animal cells. For yeasts, the signal sequence of α pheromone and the like may be employed. For *E. coli*, the signal sequence of β-lactamase and the like may be employed. In cases where the luciferase is to be accumulated in the cells, it is not necessary to ligate the signal sequence.

In cases where *E. coli* is used as the host cell and the produced luciferase is to be accumulated in the cell, it is necessary to attach a nucleotide sequence of "ATG" encoding methionine to the 5'-end of the gene which is desired to be expressed, and to ligate the resuting gene having "ATG" at the 5'-end at a site downstream of a promoter and a Shine-Delgarno sequence, also known as a ribosome binding site or an SD sequence, which function in *E. coli* cell. The SD sequence is a signal for the initiation of the protein synthesis from the "ATG" codon downstream thereof, which sequence in mRNA is recognized and bound by ribosome. The reason why the methonine is attached is that most of eukaryotic genes encoding a protein to be secreted encodes the mature protein downstream of the signal sequence for the secretion of the protein so as to produce a precursor protein having a signal peptide, and the mature protein is produced by cleaving off the signal peptide in the process of protein secretion, so that most of the eukaryotic mature proteins do not contain methionine of which the codon is indispensable to the initiation of the protein synthesis. Further, since the natural luciferase purified from *Cypridina hilgendorfii* is a mixture of two proteins of which the N-terminals are serine and threonine, respectively, and since most of the eukaryotic signal sequence is cleaved next to alanine-X-alanine and a sequence of analine-glutamic acid-alanine-proline exists in the amino acid sequence deduced from the nucleotide sequence of *Cypridina hilgendorfii* luciferase, three kinds of expression vector having a N-terminal region at the downstream of the methionine codon, which encodes the luciferase which starts from proline, serine and methionine, respectively are employed.

The transformants obtained by transforming a host cell such as animal cells, yeast cells and *E. coli* cells with each of the above-mentioned recombinant vectors are prepared by introducing the recombinant vector DNA into the host cell.

The animal cells which may be used in the present invention are not restricted. Examples of appropriate animal cells include COS-1 cell (a cell transformed with SV40 from the kidney of Africa green monkey), CHO cell (originated from the ovary of Chinese Hamster) and the like, and the COS-1 cell is preferred. The yeast cells which may be used in the present invention are not restricted. Examples of the yeasts include *Saccharomyces cerevisiae, Shizosaccaromyces pombe, Pichia pastoris* and the like. The *E. coli* cells which may be used in the present invention are not restricted and examples thereof include HB101, JM109 and the like.

The method of introducing the recombinant vector DNA into the host cell is not restricted. For example, in cases where the host cell is an animal cell, DEAE-dextran method [Mol. Cell. Biol., 5, 1188 (1985)], calcium-phosphate co-sedimentation method [Cell, 14, 725 (1978)], electroporation method [EMBO J. 1, 841 (1982)] or the like may be employed. Among these, DEAE-dextran method is preferred. In cases where the host cell is a yeast cell, protoplast method [Proc. Natl. Acad. Sci. USA, 75, 1929 (1978)] may preferably be employed. Further, in cases where the host cell is *E. coli*, calcium chloride method [J. Mol. Biol., 53, 154 (1970)] may preferably be employed.

By introducing each of the recombinant vector DNA into the host cells, novel recombinant vector DNA in which the DNA containing the gene encoding the luciferase from *Cypridina hilgendorfii* as well as transformants having the ability to produce the luciferase may be obtained.

Each of the transformants is cultured in a culture medium and the luciferase may be obtained from the culture. Any culturing medium may be employed as long as the host cell can grow therein. For example, for animal cells, Dulbecco's modified Eagle medium or the like may be employed. For yeasts, YEPD medium (20 g/l of tryptone, 10 g/l of yeast extract and 20 g/ml of glucose) or the like may be employed. For E. coli, L broth (10 g/l of trypone, 5 g/l of yeast extract and 10 g/l of sodium chloride) or the like may be employed.

Any culturing temperature may be employed as long as the cell can grow, and 15°–45° C. may usually be preferred. For animal cells and E. coli cells, 25°–40° C. is preferred and 30°–37° C. is more preferred. For yeasts, 15°–45° C. is preferred, and more preferably 20°–30° C. The culturing period is not restricted and is usually 1–10 days, preferably 3–7 days for animal cells and yeasts, and 1–3 days for E. coli.

In cases where the promoter requires an appropriate induction, for example, in cases where the promoter is the promoter of metallothionein gene for animal cells, the promoter of repressible acid phosphatase gene for yeasts or trp promoter for E. coli or the like, the expression of the promoter may be induced by the manner required for the respective promoter such as addition of an appropriate inducer, removal of an appropriate substance, changing the culturing temperature, irradiation with ultraviolet light and the like. More particularly, in cases where trp promoter is employed for E. coli, the promoter can be induced by adding IAA (indoleacrylic acid) which is an inducer of trp operon.

In cases where a trace amount of protein produced in the non-induced state adversely affects the growth of the cells, it is preferred that the expression of the promoter be repressed to a level as small as possible in the non-induced state. For example, a promoter of which expression is completely repressed in the non-induced state may be employed, or a repressor gene of the promoter may be co-employed. For example, in case of trp promoter, a recombinant plasmid having an repressor gene of the trp operon may preferably be employed. In this case, the tryptophan repressor gene (trpR) [Nucleic Acids Res. 8, 1552 (1980)] may be employed. Alternatively, the above-described method for secreting the produced protein outside the cells may be employed.

The culture is separated into the supernatant and the cells by an appropriate method such as centrifugation, and the luciferase activity in the culture supernatant or in the cell extract is measured using a luminometer or the like. Although the culture supernatant or the cell extract may be used as it is as a crude enzyme solution, if required, the luciferase may be purified by, for example, the method of F. I. Tsuji [Methods in Enzymol., 57, 364 (1978)].

The present invention will now be described in more detail by way of examples thereof.

Example 1

Construction of cDNA Library

Five grams of Cypridina hilgendorfii collected at Tateyama Bay in Chiba prefecture which was stored in frozen state was suspended in 75 ml of a solution containing 6M guanidine thiocyanate, 5 mM sodium citrate (pH 7.0) and 0.5% sodium lauryl sarkosinate, and the suspension was homogenized with Polytron Homogenizer (commercially available from Chimanetica) to disrupt the cells. Lithium chloride solution (included in a kit commercially available from Amersham) was added thereto and about 600 μg of RNA was obtained by lithium chloride co-sedimentation method. Three hundred micrograms of aliquot of the thus obtained RNA was purified by oligo(dT) cellulose column (commercially available from Colaborative Research) chromatography to obtain about 15 μg of poly(A)$^+$RNA. From 2 μg of the thus obtained poly(A)$^+$RNA, 1 μg of double-stranded DNA was obtained using a cDNA synthesis kit (commercially available from Life Technologies, Inc). The internal EcoRI site of 0.15 μg of the thus obtained double-stranded DNA was protected by EcoRI methylase and an EcoRI linker was ligated using T4 DNA ligase. The resultant was digested with EcoRI to convert both ends to EcoRI sites. The resulting DNA was inserted into the EcoRI site of λ gt10 using T4 DNA ligase and the resultant was introduced into phage particles by the in vitro packaging method. E. coli NM514 was transduced with the resulting phage to obtain a cDNA library of 1×10$^6$ PFU.

Example 2

Preparation of Oligonucleotide Probe

After lyophilizing 100 μg of Cypridina hilgendorfii luciferase which was purified by method of F. I. Tsuji [Methods in Enzymol., 57, 364 (1978)], was resuspended in 50 mM phosphate buffer (pH 7.5) containing 100 mM NaCl and further purified by gel filtration column chromatography using high performance liquid chromatography, FPLC by Pharmacia in a TSGgel G400 SW column and 50 mM phosphate (pH 7.5) containing 100 mM NaCl as eluting buffer. The luciferase activity and protein content was measured in each fraction of the column eluate. The fractions containing the peak luciferase activity were pooled and further purified by reversed phase column chromatography (RPLC) in a TSK Phenyl 5PWRP column using 2 mM $(NH_4)_2CO_3,CH_3CN$ (pH 9.0) as the mobile phase, using a Hitachi 655 A Pump-L2000 Controller 1-Pump Gradient system. The luciferase activity and protein content were determined for each fraction and fractions containing most of the luciferase activity were used for subsequent peptide analysis following lyophilyzation of the sample. The resultant was dissolved in 100 μl of 0.1M Tris-HCl (pH 7.6) containing 8M of urea and 0.14 M of 2-mercaptoethanol and the solution was incubated at 37° C. for 3 hours to pyridyl-ethylate the —SH groups. To the resultant, were added 200 μl of 0.11M Tris-HCl (pH9.0), 1 μl of 2-methylmercaptoethanol and 1 μl of 2 μg/μl lysylendopeptidase (commercially available from Wako Pure Chemicals) and the resulting mixture was incubated at 37° C. for 1 hour so as to allow the digestion. The resultant was subjected to HPLC using VYDAC 218 TP54 ($C_{18}$) (commercially available from VYDAC) to separate oligopeptides. Of the thus obtained oligopeptides, 13 oligopeptides were analyzed for the N-terminals by Amino Acid Sequencer 470A (commercially available from Applied Biosystem) to obtain the following 13 amino acid sequences:

Fragment 7-1
1                      5                          10
Thr—Cys—Gly—Ile—Cys—Gly—Asn—Tyr—Asn—Gln Fragment 7-2
1                      5                          10
Glu—Gly—Glu—Cys—Ile—Asp—Thr—Arg—Cys—Ala—

11        13
Thr—Cys—Lys

-continued

Fragment 12-1

1                 5                     10
Cys—Asn—Val—Cys—Tyr—Lys—Pro—Asp—Arg—Ile—

11
Ala

Fragment 12-2

1           5         7
Val—Ser—His—Arg—Asp—( )—Glu

Fragment 13

1              5                    10
Ala—Arg—Tyr—Gln—Phe—Gln—Gly—Pro—Met—Lys
                                              (Cys)

Fragment 18

1              5             9
Arg—Phe—Asn—Phe—Gln—Glu—Pro—Gly—Lys

Fragment 21

1              5                    10
Arg—Asp—Ile—Leu—Ser—Asp—Gly—Leu—Cys—Glu—

11              15
Asn—Lys—Pro—Gly—Lys

Fragment 23

1              5                    10
Gly—Gln—Gln—Gly—Phe—Cys—Asp—His—Ala—Trp—

11       13
Glu—Phe—Lys

Fragment 27

1              5                    10
Glu—Phe—Asp—Gly—Cys—Pro—Phe—Tyr—Gly—Asn—

11              15              18
Pro—Ser—Asp—Ile—Glu—Tyr—Cys—Lys

Fragment 38

1              5                    10
Gly—Gly—Asp—( )—Ser—Val—Thr—Leu—Thr—Met—

11              15              17
Glu—Asn—Leu—Asp—Gly—Gln—Lys

Fragment 40

1              5                    10
His—Val—Leu—Phe—Asp—Tyr—Val—Glu—Thr—Cys—

11              15                    20
Ala—Ala—Pro—Glu—Thr—Arg—Gly—Thr—Cys—Val—

21              25                    30
Leu—Ser—Gly—His—Thr—Phe—Tyr—Asp—Thr—Phe

Fragment 47

1              5                    10
Glu—Leu—Leu—Met—Ala—Ala—Asp—Cys—Tyr—( )—

11              15       16
Asn—Thr—( )—Asp—Val—Lys

Fragment 50

1              5                    10
( )—Leu—Met—Glu—Pro—Tyr—Arg—Ala—Val—Cys—

11              15                    20
( )—Asn—Asn—Ile—Asn—Phe—Tyr—Tyr—Tyr—Thr

Oligonucleotides corresponding to the following 5 oligopeptides in the above-described 13 oligopeptides were prepared using a DNA synthesizer (commercially available from Applied Biosystems). In the nucleotide sequence, "I" represents deoxyinosine.

Probe 1 (corresponding to first–6th amino acid sequence of Fragment 27)

Glu—Phe—Asp—Gly—Cys—Pro
GAA TTT GAT GGT TGT CCT
 G   C   C   C   C   C
             A       A
             G       G

3'-CTT AAA CTA CCI ACA GG-5'
    C       G   G       G

Probe II (corresponding to 6th–10th amino acid sequence of Fragment 23)

Cys—Asp—His—Ala—Trp
TGT GAT CAT GCT TGG
 C   C   C   C
         A
         G

3'-ACA CTA GTA CGI ACC-5'
    G   G   G

Probe III (corresponding to 4th–9th amino acid sequence of Fragment 47)

Met—Ala—Ala—Asp—Cys—Tyr
ATG GCT GCT GAT TGT TAT
     C   C   C   C   C
     A   A
     G   G

3'-TAC CGI CGI CTA ACA AT-5'
         G   G

Probe IV (corresponding to third–7th amino acid sequence of Fragment 50)

Met—Glu—Pro—Tyr—Arg
ATG GAA CCT TAT CGT
         C   C   C
             A   A
             G   G
                 AGA
                 G

3'-TAC CTT GGI ATA TC-5'
         C       G G

Probe V (corresponding to first–10th amino acid sequence of Fragment 13)

Ala—Arg—Tyr—Gln—Phe—Gln—Gly—Pro—Met—Lys
GCT CGT TAT CAA TTT CAA GGT CCT ATG AAA
 C   C   C   G   C   G   C   C       G
 A   A           A           A   A
 G   G           G           G   G
     AGA
     G

3'-CGI GCI ATA GTT AAA GTT CCI GGI TAC TTT-5'
    T       G   C   G   C

One microgram each of the above-described 5 oligonucleotides was dissolved in 10 μl of 50 mM Tris-HCl (pH 7.6) containing 10 mM magnesium chloride, 5 mM of dithiothreitol, 1 mM of spermidine and 100 mM potassium chloride, and then 5 μl of [γ-$^{32}$P]ATP (3,000 Ci/mmol, commercially available from Amersham), 85 μl of distilled water and 2 μl of T4 polynucleotide kinase (commercially available from Takara Shuzo) were added thereto, followed by incubation at 37° C. for 1 hour so as to carry out the labeling with $^{32}$P.

Example 3

Screening of cDNA Library by Plaque Hybridization Method

About 10,000 plaques per one plate were formed on 50 agar plates using the cDNA library prepared in Example 1. The plaques were transferred to Nylon membranes and were denatured with 0.5M sodium hydroxide/1.5M sodium chloride solution, followed by neutralization in 0.5M Tris-HCl (pH 7.0)/1.5M sodium chloride. After incubating the membranes at 80° C. for 2 hours to fix the phage DNAs to membranes, prehybridization was performed by incubating the resulting membranes in 50 mM sodium phosphate (pH 7.4) containing 0.75M sodium chloride, 5× Denhaldt's solution (0.1% bovine serum albumin, 0.1% Ficoll and 0.1% polyvinylpyrrolidone), 5 mM EDTA, 0.1% SDS and 100 μg/ml of denatured salmon sperm DNAs at 45° C. for 2 hours.

Then the resulting membranes were transferred into a fresh solution with the same composition and oligonucleotide Probe V labelled in Example 2 was added thereto to a level of 5 μCi/ml, followed by incubation at 45° C. overnight to carry out the hybridization. About 16 hours later, the membranes were washed with 6×SSC [90 mM sodium citrate (pH 7.0)/0.9M sodium chloride] containing 0.1% SDS twice for 30 minutes each at room temperature, and then twice for 30 minutes each at 45° C. After drying in air, the membranes were autoradiographed at −70° C. for 48 hours using X-OMAT AR(trademark, commercially available from Kodak).

The films were developed and 32 positive clones were obtained. Phage was grown from these positive clones on the agar plates and the phage DNAs were purified. The obtained DNAs were stored at +20° C.

Example 4

Comparison of Luciferase Protein and Primary Structure of the Gene Thereof

From the clone λ CL07 which contained the largest inserted fragment of about 1900 base pairs of the obtained 32 positive clones, the inserted fragment was cut out with restriction enzyme ECoRI and the fragment was subcloned into plasmid pUC18 to construct a recombinant plasmid pCL07 (FIG. 2). The nucleotide sequence of the 1.9 kb EcoRI fragment was determined by the usual dideoxy method. The determined nucleotide sequence is shown in FIG. 1.

By comparing the information of the obtained gene and of the protein obtained in Example 2, the protein matched with the primary structure of the gene as shown in Table 1. As a result, the nucleotide sequence of the luciferase gene from *Cypridina hilgendorfii* as well as the amino acid sequence of the protein was determined as shown in FIG. 1.

TABLE 1

Correspondence between Amino Acid Sequence and Primary Structure of Gene

| Results of Analysis of Amino Acid Sequence | Correspondence with Primary Structure of Gene |
|---|---|
| Fragment 7-1 | |
| Thr — Cys — Gly — Ile — Cys — Gly — Asn — Tyr — Asn — Gln | Thr— Cys—Gly— Ile— Cys—Gly—Asn—Tyr— Asn—Gln<br>ACA TGC GGC ATA TGT GGT AAC TAT AAT CAA |
| Fragment 7-2 | |
| Glu — Gly — Glu — Cys — Ile — Asp — Thr — Arg — Cys — Ala — | Glu—Gly— Glu—Cys—Ile— Asp—Thr— Arg—Cys—Ala—<br>GAA GGA GAA TGT ATC GAT ACC AGA TGC GCA |
| Thr — Cys — Lys | Thr— Cys—Lys<br>ACA TGT AAA |
| Fragment 12-1 | |
| Cys — Asn — Val — Cys — Tyr — Lys — Pro — Asp — Arg — Ile — | Cys—Asn—Val— Cys—Tyr— Lys— Pro— Asp—Arg—Ile—<br>TGT AAT GTC TGC TAC AAG CCT GAC CGT ATT |
| Ala | Ala<br>GCA |
| Fragment 12-2 | |
| Val — Ser — His — Arg — Asp — ( ) — Glu | Val— Ser— His— Arg—Asp—( )— Glu<br>GTT TCA CAT AGA GAT GTT GAG |
| Fragment 13 | |
| Ala — Arg — Tyr — Gln — Phe — Gln — Gly — Pro — Met — Lys<br>(Cys) | Ala— Arg—Tyr— Gln— Phe— Gln—Gly— Pro— Met—Lys<br>(Cys)<br>GCC AGA TAT CAA TTC CAG GGC CCA TGC AAA |
| Fragment 18 | |
| Arg — Phe — Asn — Phe — Gln — Glu — Pro — Gly — Lys | Arg—Phe— Asn—Phe— Gln—Glu— Pro— Gly—Lys<br>AGA TTT AAT TTT CAG GAA CCT GGT AAA |
| Fragment 21 | |
| Arg — Asp — Ile — Leu — Ser — Asp — Gly — Leu — Cys — Glu — | Arg—Asp—Ile— Leu—Ser— Asp—Gly—Leu—Cys—Glu—<br>CGA GAC ATA CTA TCA GAC GGA CTG TGT GAA |
| Asn — Lys — Pro — Gly — Lys | Asn—Lys—Pro— Gly—Lys<br>AAT AAA CCA GGG AAG |
| Fragment 23 | |
| Gly — Gln — Gln — Gly — Phe — Cys — Asp — His — Ala — Trp — | Gly—Gln—Gln— Gly—Phe—Cys—Asp—His— Ala—Trp—<br>GGA CAG CAA GGA TTC TGT GAC CAT GCT TGG |
| Glu — Phe — Lys | Glu—Phe—Lys<br>GAG TTC AAA |
| Fragment 27 | |

TABLE 1-continued

Correspondence between Amino Acid Sequence and Primary Structure of Gene

| Results of Analysis of Amino Acid Sequence | Correspondence with Primary Structure of Gene |
|---|---|
| Glu—Phe—Asp—Gly—Cys—Pro—Phe—Tyr—Gly—Asn— | Glu—Phe—Asp—Gly—Cys—Pro—Phe—Tyr—Gly—Asn<br>GAG TTC GAC GGC TGC CCA TTC TAC GGG AAT |
| Pro—Ser—Asp—Ile—Glu—Cys—Lys | Pro—Ser—Asp—Ile—Glu—Tyr—Cys—Lys<br>CCT TCT GAT ATC GAA TAC TGC AAA |
| Fragment 38<br>Gly—Gly—Asp—( )—Ser—Val—Thr—Leu—Thr—Met— | Gly—Gly—Asp—( )—Ser—Val—Thr—Leu—Thr—Met—<br>GGT GGC GAC TGG TCT GTA ACC CTC ACC ATG |
| Glu—Asn—Leu—Asp—Gly—Gln—Lys | Glu—Asn—Leu—Asp—Gly—Gln—Lys<br>GAG AAT CTA GAT GGA CAG AAG |
| Fragment 40<br>His—Val—Leu—Phe—Asp—Tyr—Val—Glu—Thr—Cys— | His—Val—Leu—Phe—Asp—Tyr—Val—Glu—Thr—Cys—<br>CAC GTC CTT TTC GAC TAT GTT GAG ACA TGC |
| Ala—Ala—Pro—Glu—Thr—Arg—Gly—Thr—Cys—Val— | Ala—Ala—Pro—Glu—Thr—Arg—Gly—Thr—Cys—Val—<br>GCT GCA CCG GAA ACG AGA GGA ACG TGT GTT |
| Leu—Ser—Gly—His—Thr—Phe—Tyr—Asp—Thr—Phe— | Leu—Ser—Gly—His—Thr—Phe—Tyr—Asp—Thr—Phe—<br>TTA TCA GGA CAT ACT TTC TAT GAC ACA TTC |
| Fragment 47<br>Glu—Leu—Leu—Met—Ala—Ala—Asp—Cys—Tyr—( )— | Glu—Leu—Leu—Met—Ala—Ala—Asp—Cys—Tyr—( )—<br>GAG CTT CTG ATG GCC GCA GAC TGT TAC TGG |
| Asn—Thr—( )—Asp—Val—Lys | Asn—Thr—( )—Asp—Val—Lys<br>AAC ACA TGG GAT GTA AAG |
| Fragment 50<br>( )—Leu—Met—Glu—Pro—Tyr—Arg—Ala—Val—Cys— | ( )—Leu—Met—Glu—Pro—Tyr—Arg—Ala—Val—Cys—<br>GGT CTC ATG GAG CCA TAC AGA GCT GTA TGT |
| ( )—Asn—Asn—Ile—Asn—Phe—Tyr—Tyr—Tyr—Thr | ( )—Asn—Asn—Ile—Asn—Phe—Tyr—Tyr—Tyr—Thr<br>CGT AAC AAT ATC AAC TTC TAC TAT TAC ACT |

Example 5

Insertion of Luciferase cDNA into Expression Vector pSVL Containing SV40 Late Promoter One microgram of the above-mentioned 1.9 kb EcORI fragment encoding luciferase from *Cypridina hilgendorfii* obtained in Example 4 was treated with 5 units of *E. coli* DNA polymerase I large fragment (commercially available from Takara Shuzo) in the presence of 1.5 mM each of dATP, dTTP, dCTP and dGTP to repair the ends of the fragment. On the other hand, vector pSVL (an expression vector containing SV40 late promoter, commercially available from Pharmacia) was digested with restriction enzyme SmaI.

Then the 1.9 kb fragment (0.3 µg) of which the ends were repaired and the SmaI digest of pSVL (0.1 µg) were ligated by T4 DNA ligase, and *E. coli* HB101 competent cells (commercially available from Takara Shuzo) were transformed with the resulting reaction mixture to obtain a recombinant plasmid in which the 1.9 kb fragment was inserted. The obtained recombinant plasmid was named pSVLCL5 (FIG. 3).

Example 6

Production of Luciferase from *Cypridina hilgendorfii* by COS-1 Cell

The expression vector pSVLCL5 (10 µg) constructed in Example 5 was introduced into COS-1 cells by DEAE-dextran method [Mol. Cell. Biol. 5, 1188 (1985)]. On the other hand, as a control, pSVL (10 µg) was introduced in the same manner into COS-1 cells.

These cells were cultured in 10 ml of Dulbecco's modified Eagle Medium (commercially available from Nissui Pharmaceuticals) containing 10% fetal bovine serum in a culturing flask of 25 cm² in the presence of 5% $CO_2$ at 37° C. for 5 days. During the culturing and after the culturing, 1 ml each of the culture liquid was recovered and was centrifuged at 3,000 rpm for 10 minutes at 4° C. The supernatant of each of them was collected to obtain culture supernatants.

After the culturing, cells were peeled from the flask by trypsin treatment and were washed with 1 ml of PBS (–) (commecially available from Nissui Pharmaceuticals). The washings were centrifuged at 3,000 rpm for 10 minutes at 4° C. and the supernatant was discarded. This operation was further repeated twice and the cells were suspended in 200 µl of PBS(–). A freeze-thaw cycle was repeated three times to obtain a cell extract.

Example 7

Assay of Luciferase Activity Produced by Animal Cells

The luciferase activities in the culture supernatants described in Example 6 were measured by the following method and the results are shown in Table 2: That is, 30 µl of the culture supernatant and 270 µl of a measuring buffer [100 mM sodium phosphate (pH 7.0)/200 mM sodium chloride] were mixed. To the mixture, was added 2 µl of 33 µM *Cypridina hilgendorfii* luciferin and the number of photons generated was counted immediately for 30 seconds using a luminometer (Lumac L2010). The luminescent intensity is indicated in terms of the average number of photons per one second. The number of generated photons were measured in the same manner for the culture supernatant of COS-1 cell in which pSLV was introduced as a control.

The luciferase activity in the cell extract described in Example 6 was measured by the following method and the results are shown in Table 2: That is, 10 µl of the cell fraction prepared in Example 6 and 290 µl of the above-described measuring buffer were mixed and 2 µl of 33 µM *Cypridina hilgendorfii* luciferin was added thereto, followed by the measurement of luciferase activity in the same manner as in the measurement for the culture supernatants.

TABLE 2

| plasmid | Activity of Luciferase (× 10⁵ cps/ml) | | | | | |
|---|---|---|---|---|---|---|
| | Extracellular | | | | Intracellular | |
| | 24 hours | 48 hours | 72 hours | 96 hours | 120 hours | 120 hours |
| (a) pSVLCL5 (No. 1) | 2.2 | 4.0 | 4.3 | 4.6 | 5.2 | 1.2 |
| (b) pSVLCL5 (No. 2) | 2.3 | 5.8 | 8.3 | 9.0 | 10.5 | 3.0 |
| (c) pSVLCL5 (No. 3) | 2.1 | 3.1 | 3.8 | 4.1 | 5.5 | 0.8 |
| (d) pSVLCL5 (No. 4) | 2.3 | 4.0 | 5.5 | 5.7 | 6.7 | 1.4 |
| (e) pSVL (control) | 2.0 | 2.5 | 2.3 | 2.3 | 2.1 | 0.2 |

Example 8

Synthesis of Oligonucleotides for Yeast Expression Vector and Annealing

Luciferase proteins having the amino acid sequence starting from the 29th amino acid proline of the amino acid sequence shown in FIG. 1 (YP type), from the 30th amino acid serine (YN type), from the 31st amino acid serine (YS type) and from the 32nd amino acid threonine (YT type), respectively, were prepared since (1) the wild type luciferase purified from *Cypridina hilgendorfii* is a mixture of two proteins of which the N-terminal is either the 31st amino acid serine in the amino acid sequence shown in FIG. 1 or the 32nd amino acid threonine; (2) an amino acid sequence having the characteristics of the signal sequence for the secretion of proteins exists at the N-terminal of the amino acid sequence of the luciferase, which is deduced from the nucleotide sequence of the cDNA; and since (3) the signal sequence is cleaved off at the downstream of the sequence of alanine-X-alanine in most of eukaryotes and *Cypridina hilgendorfii* luciferase has a sequence of alanine-glutamic acid-alanine-proline. To ligate the proteins downstream of the signal sequence of the a pheromone, the following 10 oligonucleotides were synthesized.

| YP-1 | 5'-CCTTCAAGTACTCCA-3' |
| YP-2 | 5'-CTGTTGGAGTACTTGAAGG-3' |
| YS-1 | 5'-AGTACACCA-3' |
| YS-2 | 5'-CTGTTGGTGTACT-3' |
| YT-1 | 5'-ACTCCA-3' |
| YT-2 | 5'-CTGTTGGAGT-3' |
| YN-1 | 5'-TCGTCGACACCA-3' |
| YN-2 | 5'-CTGTTGGTGTCGACGA-3' |
| U-1 | 5'-ACAGTCCCAACATCTTGTGAAGCTAAAGAAGGAGAATGTAT-3' |
| U-2 | 5'-CGATACATTCTCCTTCTTTAGCTTCACAAGATGTTGGGA-3' |

5'-Ends of the synthetic oligonucleotides YP-2, YS-2, YT-2, YN-2 and U-2 were phosphorylated by T4 DNA kinase. That is, 300 pmol each of the oligonucleotides was reacted in 20 µl of a reaction mixture [50 mM Tris-HCl (pH 7.6) containing 10 mM magnesium chloride, 0.1 mM spermidine, 5 mM dithiothreitol and 0.1 mM EDTA] in the presence of 10 units of T4 DNA kinase (commercially available from Takara Shuzo) at 37° C. for 1 hour and then the reaction mixture was heated at 70° C. for 5 minutes, followed by storage at –20° C.

The annealing of each oligonucleotide was performed as follows:

For YP type, 50 pmol each of YP-1, phosphorylated YP-2, U-1 and phosphorylated U-2 were mixed. For YS type, 50 pmol each of YS-1, phosphorylated YS-2, U-1 and phosphorylated U-2 were mixed. For YT type, 50 pmol each of YT-1, phosphorylated YT-2, U-1 and phosphorylated U-2 were mixed. For YN type, 50 pmol each of YN-1, phosphorylated YN-2, U-1 and phosphorylated U-2 were mixed. Each mixture was heated at 70° C. for 5 minutes and then the power of the incubator was shut off to leave the mixture to stand until the temperature is lowered to 42° C.

Example 9

Insertion of Luciferase cDNA into Expression Vector pMFα8 Containing the Promoter of Yeast α Pheromone Gene The synthetic oligomers described in Example 8 were respectively inserted into *Cypridina hilgendorfii* luciferase cDNA at the ClaI site to construct luciferase cDNAs having StuI site at the 5'-end, from which 28, 29, 30 and 31 amino acids from the N-terminal were cut off, respectively.

Figures 4A, 4B:
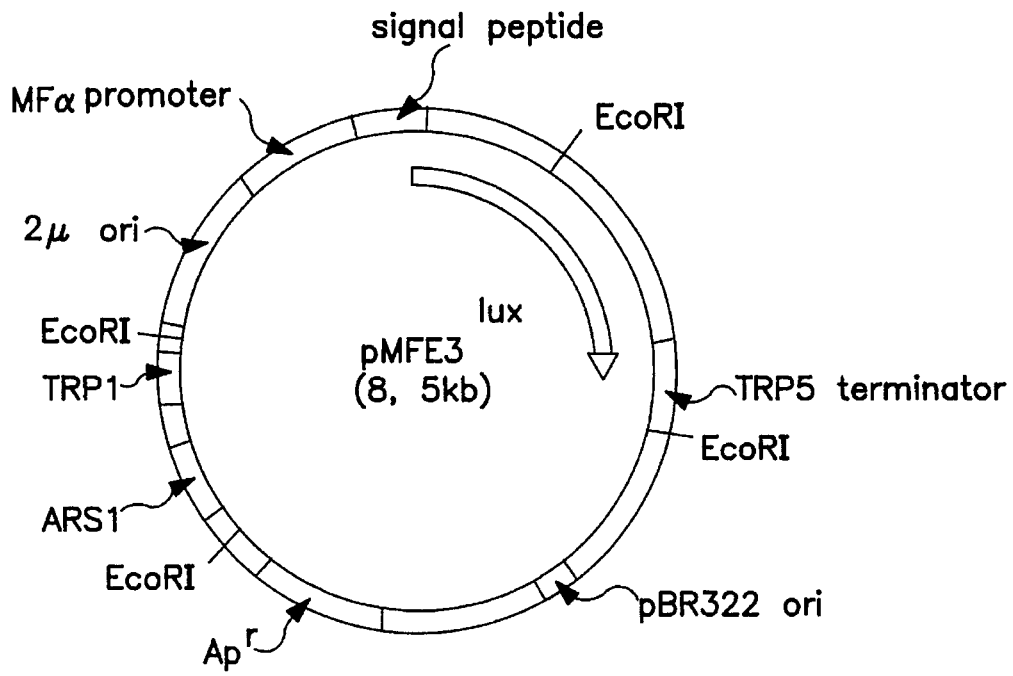
FIG. 4a shows restriction maps of expression vectors pMEF3A, pMFE3B, pMFE3C and pMFE3D of the luciferase from *Cypridina hilgendorfii* for yeast cells
FIG. 4b shows the nucleotide sequence of the region in the vicinity of the junction region of α pheromone gene and cDNA of the luciferase, as well as the amino acid sequence thereof.

The expression vector pMFα8 for yeasts [Gene, 3, 155 (1985): ATCC 37418] was digested with restriction enzyme StuI immediately downstream of the region encoding the leader sequence of the a pheromone gene and the above-mentioned luciferase cDNA was inserted therein. The thus constructed expression vectors were named pMEF3A (YP type), pMEF3B (YS type), pMEF3C (YT type) and pMEF3D (YN type), respectively (FIG. 4a).

The nucleotide sequence in the vicinity of the Junction region between the α pheromone gene and luciferase cDNA of each expression vector was checked by the usual dideoxy method using a sequence in the luciferase cDNA, 5'-TATAAATGGTCCAAGGA-3', as a primer to confirm that the cDNAs were inserted correctly. The nucleotide sequences in the vicinity of the junction region between the α pheromone gene and luciferase cDNA of pMFE 3A, pMFE3B, pMFE3C and pMFE3D are shown in FIG. 4b.

Example 10

Insertion of Luciferase cDNA into Expression Vector p103 Containing the Promoter of Yeast GAL1 Gene The two EcoRI fragments of 1.3 kb and 0.6 kb were cut out from λ CL07 obtained in Example 3 and were respectively subcloned to plasmid pUC18 to construct plasmids pCL0712 and pCL0742, respectively. pCL07 (1 µg) and pCL0712 (1 µg) were cut with HindIII and BglII, and a DNA fragment containing the N-terminal of the luciferase was purified from pCL07 and a DNA fragment containing the C-terminal of the luciferase was purified from pCL0712. The two fragments were subcloned to a plasmid pSPT18 (commercially available from Boehringer-Mannheim) at the HindIII site thereof, and the obtained plasmid was named pSTCL81.

The pSTCL81 (1 µg) was digested with BamHI and the total cloned cDNA sequence was obtained as BamHI fragment.

Figure 5:
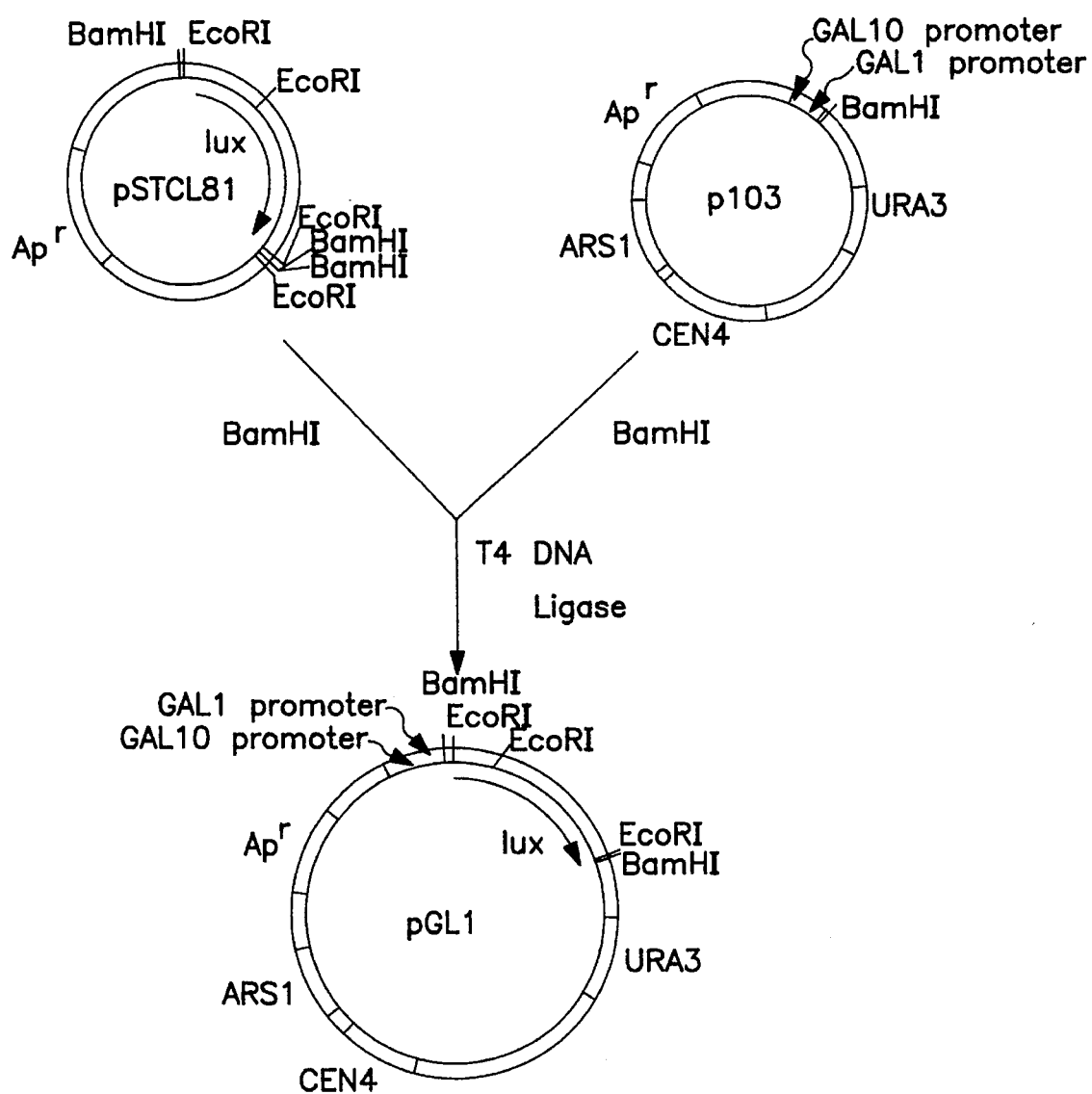
FIG. 5 shows a construction of an expression vector pGL1 of the luciferase from *Cypridina hilgendorfii* for yeast cells.

On the other hand, about 1 µg of expression vector p103 [containing a polylinker including BamHI site at the downstream of the GAL1 promoter of *Saccharomyces cerevisiae* (Mol. Cell. Biol., 4, 1440 (1984)); presented by Assistant Professor Shun Harajima of Osaka University] was digested with BamHI and the resultant was ligated with about 0.1 µg of the above-mentioned cDNA fragment to construct an expression vector pGL1 in which the luciferase cDNA was inserted downstream of the GAL1 promoter (FIG. 5).

Example 11

Production of Luciferase from *Cypridina hilgendorfii* by Yeast

Ten micrograms each of the expression vectors pMFE3A, pMFE3B, pMFE3C and pMFE3D prepared in Example 9 were introduced into *Saccharomyces cerevisiae* 20B-12 strain [Gene, 37, 155 (1985)] by the protoplast method [Proc. Natl. Acad. Sci. USA, 75, 1929 (1978)].

These transformants were cultured at 30° C. for 3 days in 100 ml of YEPD medium contained in a 1-liter culturing flask. During the culturing and after the culturing, 5 ml each of the culture was collected and was centrifuged at 4° C. for 10 minutes at 3000 rpm. The supernatants were collected to obtain culture supernatants.

The cells harvested from one milliliter of each culture were washed with 5 ml of sterilized distilled water, and the cells were suspended in 1 ml of 50 mM sodium phosphate (pH 7.5) containing 0.1% Triton X-100. To this suspension, 1 ml of a glass beads (0.45 mm diameter) suspension was added and the mixture was left to stand at 0° C. for 5 minutes while sometimes vigorously agitating the mixture with a mixer. The glass beads were separated by gentle centrifugation, and the supernatant was transferred to a 1.5 ml Eppendorf's tube, followed by centrifugation at 15,000 rpm for 5 minutes. The obtained supernatant was used as the cell extract.

Example 12

Production of Luciferase from *Cypridina hilgendorfii* by Yeast

The expression vector pGL1 (10 µg) was introduced into *Saccharomyces cerevisiae* YSH2676 strain ((a) ura3–52 leu2-3 leu2-112 trp1 pho3 pho5 his1-29) by the protoplast method as in Example 11.

The transformant was cultured at 30° C. for 2 days in 100 ml of a medium (1% yeast extract, 2% peptone and 2% galactose) in a 1-liter culturing flask. During the culturing and after the culturing, 5 ml each of the culture was collected and was centrifuged at 3,000 rpm for 10 minutes at 4° C. The supernatants were recovered and were used as the culture supernatant.

Further, the cell extract was prepared in the same manner as in Example 11.

Example 13

Assay of Activity of Luciferase Produced by Yeast

The luciferase activities in the culture supernatants described in Example 11 were measured in the same manner as in the measurement for the culture supernatants of the animal cells described in Example 7. The results are shown in Table 3. As a control, the number of generated photons of the culture supernatant of *S. cerevisiae* 20B-12 strain into which pMFα8 was introduced was also counted in the same manner.

The luciferase activity in the yeast cells described in Example 11 were performed by the method described below and the results are shown in Table 3. That is, 10 µl of the cell extract prepared in Example 11 and 290 µl of the above-described measuring buffer were mixed and 2 µl of 33 µM *Cypridina hilgendorfii* luciferin was added thereto, followed by the measurement of the luciferase activity in the same manner as in the measurement for the culture supernatants.

TABLE 3

| | plasmid | | Activity of Luciferase ($\times 10^5$ cps/ml) | | | | |
|---|---|---|---|---|---|---|---|
| | | | 12 hours | 21 hours | 38 hours | 47 hours | 64 hours |
| (a) | pMFE3A | Intracellular | <0.01 | <0.01 | 0.01 | 0.02 | 0.01 |
| | | Extracellular | 0.05 | 0.02 | 4.84 | 13.47 | 2.11 |
| (b) | pMFE3B | Intracellular | <0.01 | <0.01 | 0.02 | 0.01 | <0.01 |
| | | Extracellular | 0.06 | 0.20 | 6.22 | 2.73 | 1.02 |
| (C) | pMFE3C | Intracellular | <0.01 | <0.01 | 0.02 | 0.01 | 0.01 |
| | | Extracellular | 0.10 | 0.21 | 2.76 | 0.79 | 0.89 |

TABLE 3-continued

| plasmid | | Activity of Luciferase ($\times 10^5$ cps/ml) | | | | |
|---|---|---|---|---|---|---|
| | | 12 hours | 21 hours | 38 hours | 47 hours | 64 hours |
| (d) pMFE3D | Intracellular | <0.01 | <0.01 | 0.02 | 0.01 | 0.01 |
| | Extracellular | 0.06 | 0.21 | 3.97 | 0.76 | 1.02 |
| (e) control | Intracellular | <0.01 | <0.01 | <0.01 | 0.01 | <0.01 |
| | Extracellular | 0.06 | 0.04 | 0.05 | 0.06 | 0.11 |

Example 14

Assay of Activity of Luciferase Produced by Yeast

The luciferase activity in the culture supernatants were determined in the same manner as in the measurement for the culture supernatant of the animal cells described in Example 7, and the results are shown in Table 4. As a control, the number of generated photons of the culture supernatant of S. cerevisiae YSH2676 strain into which p103 was introduced was also counted in the same manner.

The luciferase activity in the yeast cells described in Example 12 were measured in the same manner as in Example 13, and the results are shown in Table 4.

TABLE 4

| clone No. | | Activity of Luciferase ($\times 10^5$ cps/ml) | | |
|---|---|---|---|---|
| | | 20 hours | 43 hours | 51 hours |
| (a) No. 1 | Intracellular | 0.06 | 0.07 | 0.07 |
| | Extracellular | 0.53 | 7.28 | 7.71 |
| (b) No. 2 | Intracellular | 0.04 | 0.06 | 0.07 |
| | Extracellular | 0.44 | 3.04 | 3.49 |
| (c) No. 3 | Intracellular | 0.07 | 0.07 | 0.06 |
| | Extracellular | 0.40 | 3.00 | 4.70 |
| (d) No. 4 | Intracellular | 0.05 | 0.10 | 0.09 |
| | Extracellular | 0.92 | 5.89 | 6.27 |
| (e) No. 5 | Intracellular | 0.06 | 0.08 | 0.05 |
| | Extracellular | 0.50 | 2.52 | 2.47 |
| (f) control | Intracellular | 0.01 | n.t. | n.t. |
| | Extracellular | 0.08 | 0.13 | 0.03 |

Example 15

Synthesis of Oligonucleotides for E. coli Expression Vector and Annealing

To construct expression vectors containing a gene encoding the luciferase of which the amino acid sequence starts from the sequence of methonine-proline (EP type), methionine-serine (ES type) or methionine-threonine (ET type) at a site downstream of the promoter and an SD sequence of the E. coli tryptophan synthesis gene (trp) operon, the following 6 oligonucleotides were synthesized:

| EP-1 | 5'-CGATGCCGTCAAGTACACCA-3' |
| EP-2 | 5'-CTGTTGGTGTACTTGACGGCAT-3' |
| ES-1 | 5'-CGATGAGTACACCA-3' |
| ES-2 | 5'-CTGTTGGTGTACTCAT-3' |
| ET-1 | 5'-CGATGACACCA-3' |
| ET-2 | 5'-CTGTTGGTGTCAT-3' |

The N-terminals of 300 pmol each of the synthetic oligonucleotides EP-2, ES-2 and ET-2 as well as U-2 prepared in Example 8 were phosphorylated using T4 DNA kinase as in Example 8 and the phosphorylated oligonucleotides were stored at +20° C.

For EP type, 50 pmol each of EP-1, phosphorylated EP-2, U-1 and phosphorylated U-2 were mixed. For ES type, 50 pmol each of ES-1, phosphorylated ES-2, U-1 and phosphorylated U-2 were mixed. For ET type, 50 pmol each of ET-1, phosphorylated ET-2, U-1 and phosphorylated U-2 were mixed. Each of the mixtures was subjected to annealing as in Example 8.

Example 16

Insertion of Luciferase cDNA into Expression Vector pMT1 containing E. coli trp Promoter Expression vector pMT-1 [originated from pKM6 (Japanese Laid Open Patent Application (Kokai) No. 61-247387)] having the promoter and an SD sequence of E. coli tryptophan operon (trp) was digested with restriction enzymes SmaI, ClaI and PvuII.

On the other hand, the expression vector pCL07 prepared in Example 3 was digested with SmaI and ClaI, and a DNA fragment containing luciferase cDNA downstream from the ClaI site was separated and purified by the agarose gel electrophoresis method.

Using T4 DNA ligase (commercially available from Takara Shuzo), 0.1 μg each of the pMT-1 digest and the purified fragment from pCL07 were ligated and the resultant was digested again by restriction enzyme SmaI. E. coli HB101 competent cells (commercially available from Takara Shuzo) was transformed with the resultant to construct a plasmid pMT-CL07. This plasmid had a part of the luciferase cDNA of the region downstream from the ClaI site, at a site downstream of the trp promoter/SD sequence.

The plasmid pMT-CL07 was digested with restriction enzyme ClaI and 0.1 μg of the obtained digest and 5 μl of the synthetic DNA construct in Example 15 were ligated by T4 DNA ligase to construct expression vectors containing the luciferase gene starting from the codons of methionine-proline (EP type), methionine-serine (ES type) or methionine-threonine (ET type), at a site downstream of the trp promoter/SD sequence. The thus constructed plasmids were named pMT-CLP, pMT-CLS and pMT-CLT, respectively.

The nucleotide sequence in the vicinity of the Junction region between the SD sequence and luciferase gene of each expression vector was checked by the usual dideoxy method using a sequence of 5'-TATAAATGGTCCAAGGA-3' in the luciferase cDNA as a primer to confirm that the cDNA was inserted correctly.

Figure 6:
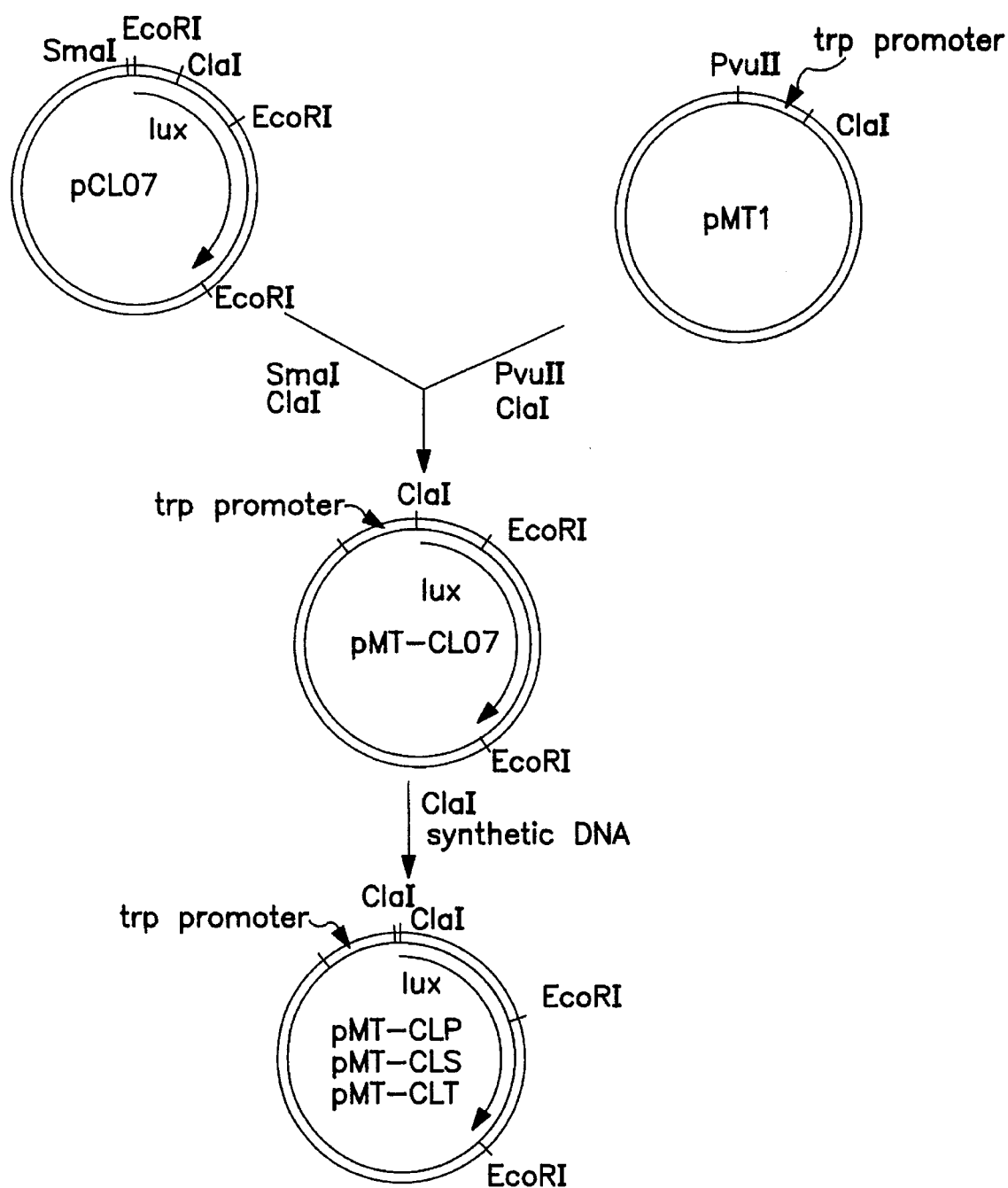
FIG. 6 shows a construction process of expression vectors pMT-CLP, pMT-CLS and pMT-CLT of the luciferase from *Cypridina hilgendorfii* for *E. coli*.

The restriction maps of pMT-CLP, pMT-CLS and pMT-CLT as well as the confirmed nucleotide sequences are shown in FIG. 6.

Example 17

Production of Luciferase from *Cypridina hilgendorfii* by *E. coli*

*E. coli* HB101 was transformed with each expression vector prepared in Example 16, and each transformant was cultured statically in 5 ml of L broth (containing 100 mg/l of ampicillin) overnight at 37° C. On the next day, 1 ml of the culture fluid was collected and was suspended in 50 ml of a synthetic medium [2×M9-casamino acids medium (6 g/l of potassium dihydrogen phosphate, 12 g/l of disodium hydrogen-phosphate, 10 g/l of casamino acids, 10 g/l of sodium chloride, 1 g/l of ammonium chloride), 1 mg/l of thiamine-HCl, 250 mg/l of magnesium sulfate, 1% glucose and 100 mg/l of ampicillin, and the resultant was cultured overnight at 25° C. with shaking. On the morning of the next day, IAA (final concentration of 20 mg/l) and glucose (final concentration of 1%) were added and the pH thereof was adjusted to 7.5 with 12.5% ammonia water. The culture was continued for 3 hours at 25° C. After 3 hours, IAA, glucose and ammonia water were added in the same manner and the culture was continued for another 3 hours. After culturing, 8 ml of the culture fluid was centrifuged to collect the cells, and the cells were suspended in 0.5 ml TE buffer [10 mM Tris-HCl (pH 8.0)/1 mM EDTA]. A freeze-thaw cycle was repeated 3 times using warm water at 42° C. and dry ice/acetone to disrupt the cells and the resultant was centrifuged at 10,000 rpm for 10 minutes. The obtained supernatant was used as a crude enzyme solution.

Example 18

Assay of Activity of Luciferase Produced by *E. coli*

The luciferase activity in the crude enzyme solution prepared in Example 17 was measured by the method described below and the results are shown in Table 5. That is, 150 µl of the crude enzyme solution and 150 µl of the measuring buffer and 2 µl of 33 µM *Cypridina hilgendorfii* luciferin were mixed and the number of generated photons were counted for 30 seconds. The results are shown in Table 5. As a control, the number of the generated photons were counted for *E. coli* HB101 in which pMT-CLR (a plasmid in which the synthetic DNA is inserted in the wrong orientation).

TABLE 5

| Plasmid | Luciferase Activity (cps) |
| --- | --- |
| (a) pMT-CLP | 1200 |
| (b) pMT-CLS | 870 |
| (c) pMT-CLT | 540 |
| (d) pMT-CLR (control) | 200 |

INDUSTRIAL APPLICABILITY

The luciferase from *Cypridina hilgendorfii* provides a luminescent system with very high luminescence intensity. Therefore, the enzyme may be attached to an antibody molecule and used for EIA (enzyme immunoassay). Alternatively, the enzyme may be attached to DNA/RNA molecule which may be used in the DNA probe method. Thus, the wide use of the enzyme for various assays is expected.

By the present invention, the primary structure of the cDNA encoding the luciferase from *Cypridina hilgendorfii* was determined and the primary structure of the luciferase was also identified. By culturing the animal cells, yeasts or *E. coli* containing the expression vector of the luciferase of the present invention in a large scale, the luciferase may be supplied constantly in a large amount at a low cost.

It is claimed:

1. An isolated DNA fragment comprising a sequence encoding a luciferase of Cypridina hilgendorfii having an amino acid sequence set forth in FIG. 1 selected from the group consisting of positions 1 through 555, positions 29 through 555, positions 30 through 555, positions 31 through 555, and positions 32 through 555.

2. The DNA sequence of claim 1 having the nucleotide sequence shown in FIG. 1 and which encodes a luciferase of *Cypridina hilgendorfii*.

3. A vector DNA comprising the DNA sequence of claim 1 encoding a luciferase of *Cypridina hilgendorfii* ligated at a site operably linked downstream of a promoter which can be expressed in a host cell.

4. A vector DNA comprising the DNA sequence of claim 1 encoding a luciferase of *Cypridina hilgendorfii* ligated at the site operably linked downstream of a promoter and a ribosome binding site, which can be expressed in *E. coli*.

5. A transformant prepared by transforming a host cell selected from the group consisting of an animal cell, a yeast cell and an *E. coli* cell with a vector according to claim 3.

6. A process for producing luciferase comprising culturing the transformant according to claim 5 and thereafter recovering said luciferase from the culture.

* * * * *